Figure 5:
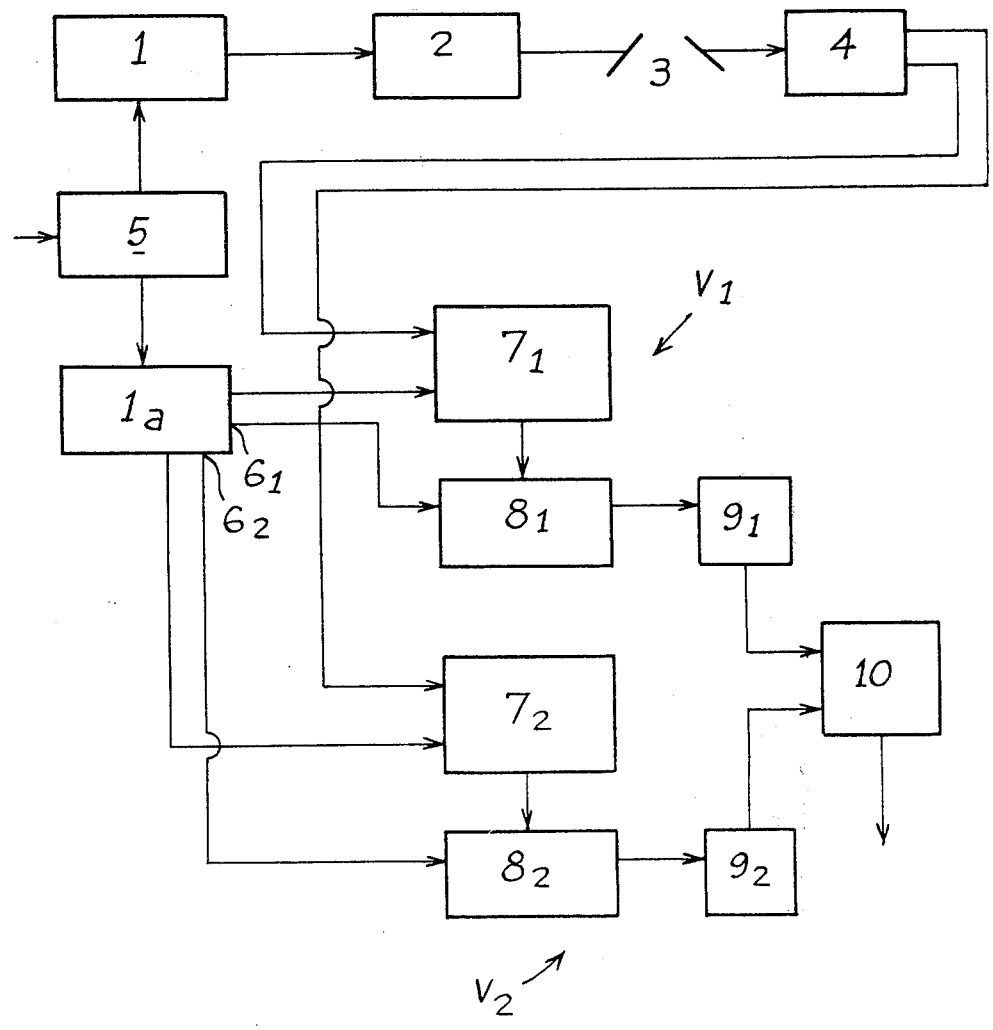

United States Patent [19]
Cathignol et al.

[11] 4,320,765
[45] Mar. 23, 1982

[54] DOPPLER PSEUDORANDOM NOISE VELOCIMETERS

[75] Inventors: Dominique Cathignol, Genas; Claude Fourcade, Tassin la Demi Lune; Jean-Yves Chapelon, Saint-Etienne, all of France

[73] Assignee: Institut National de la Sante et de la Recherche Medicale - I.N.S.E.R.M., France

[21] Appl. No.: 112,528

[22] Filed: Jan. 16, 1980

[30] Foreign Application Priority Data

Jan. 19, 1979 [FR] France ................. 79 02136

[51] Int. Cl.³ ............................................. A61B 10/00
[52] U.S. Cl. ............................... 128/663; 73/861.25; 367/90; 367/100
[58] Field of Search .................. 128/663; 73/861.05, 73/861.25; 367/90, 100

[56] References Cited

U.S. PATENT DOCUMENTS

| | | | |
|---|---|---|---|
| 3,158,830 | 11/1964 | Clay | 367/100 |
| 3,631,490 | 12/1971 | Palmiere | 367/100 |
| 3,940,731 | 2/1976 | Cooper et al. | 128/663 |
| 3,953,823 | 4/1976 | Katakura | 128/663 X |

OTHER PUBLICATIONS

Siegel, M. et al., "Doppler Flow Visualization Using Large Time-Bandwidth Signals," Acoustic Holography, vol. 7, 1978 Plenum Press, pp. 347-357.
Reed, E. W. et al., "The Measurement of Pulsating Gas Flow Velocities Using Pseudo-random Pressure Pulses", Measurement & Control, Oct. 4-7, 1972.
Waag, R. C. et al., "Instrumentation for Non-Invasive Cardiac Chamber Flow Rate Measurement", IEEE UTS Symposium, Boston, Oct. 1972.
Jethwa, C. P. et al., "Blood Flow Measurements Using Ultrasonic Pulsed Random Signal Doppler System", IEEE Trans. on Sonics & Ultransonics, vol. Su-22, No. 1, pp. 1-11, Jan. 1975.
Bendiak, P. J. et al., "Ultrasonic Random-Signal Flow Measurement System" Jrnl Acoustic Soc. America, vol. 56, No. 3, Sep. 1974, pp. 860-865.

*Primary Examiner*—Robert W. Michell
*Assistant Examiner*—Francis J. Jaworski
*Attorney, Agent, or Firm*—Lerner, David, Littenberg & Samuel

[57] ABSTRACT

This invention is directed to improved pseudorandom noise velocimeters and methods therefor, using the Doppler effect, to enable the external measurement of the speed of a moving target within a fixed conveying medium. In accordance with a preferred embodiment of the present invention a continuous pseudorandom ultrasonic noise signal formed by a repetitive code C having n different elementary segments S is radiated. Correlation between a received echo and the delayed radiated signal is accomplished by proceeding successively for each elementary segment, using a different measuring band, for a period corresponding to the period of each segment. The correlation values thus obtained are then stored and thereafter a Doppler low frequency curve is reconstituted by regrouping the correlation values corresponding to the different elementary segments of the repetitive code.

7 Claims, 7 Drawing Figures

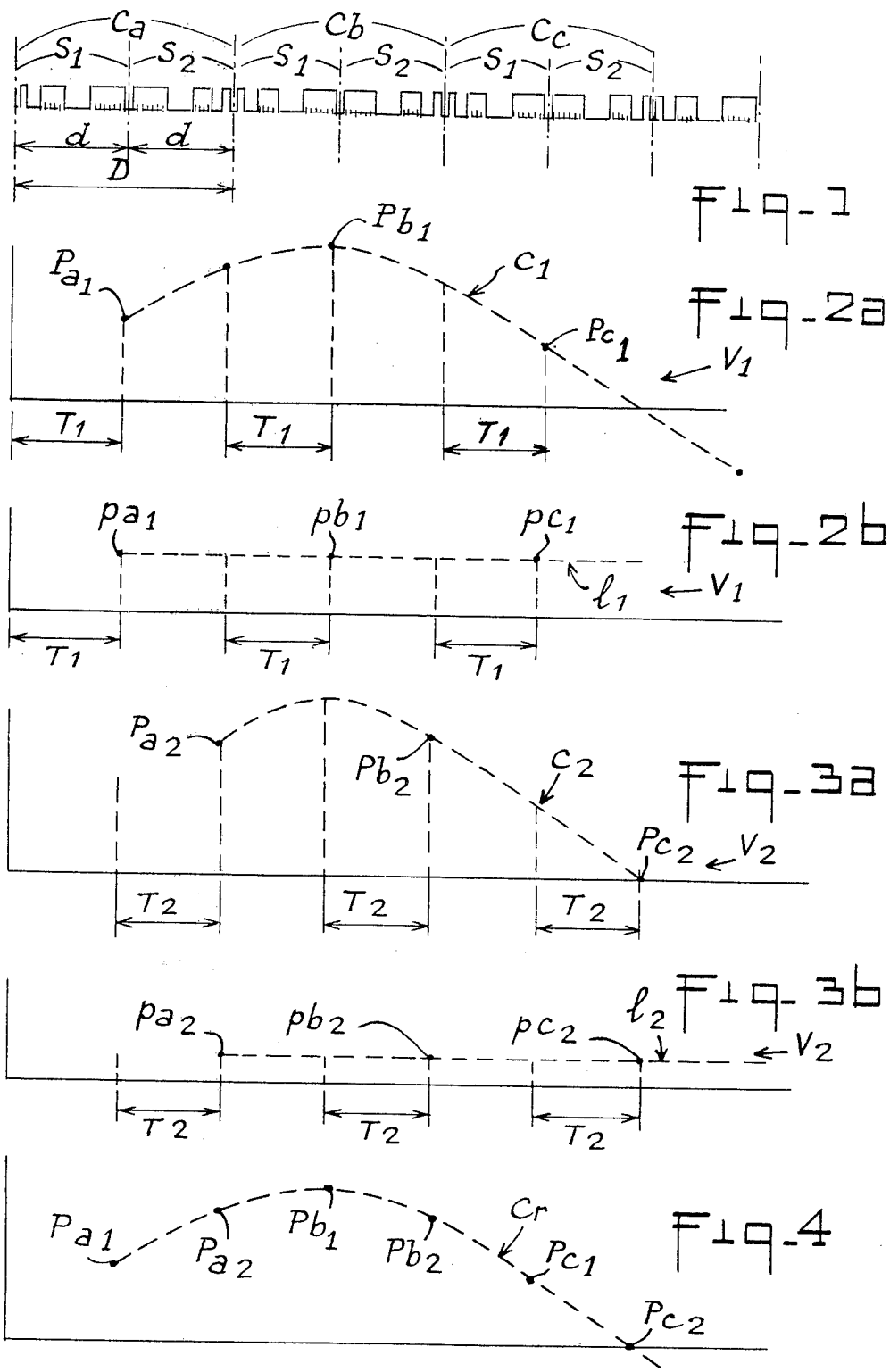

DOPPLER PSEUDORANDOM NOISE VELOCIMETERS

The present invention relates to supersonic velocimeters, using the DOPPLER effect, for measuring the speed of a moving target inside a medium having fixed targets, and more particularly, in a preferred application to measuring the velocity of the blood, in the arteries for example, it relates to an apparatus of the so-called external type, as as opposed to an apparatus the implantation of which into the patient necessitates an operation which is a traumatizing experience for him.

In the aforesaid application, DOPPLER velocimeters have already been proposed, which use the fact that the frequency of ultrasounds reflected by a moving target differs from the transmission frequency of a quantity proportional to the velocity of the target.

Continuous transmission velocimeters have already been proposed for measuring the flow velocity of the blood, and also, pulsed transmission velocimeters, which, in addition, give the distance of the reflecting target.

A pulsed transmission velocimeter recurrently radiates a wave train of n sinusoids the waveform of which is a pulse of width $\tau e$. The distance resolution of such an apparatus is in inverse ratio to the width of the said pulse. Consequently, any possible improvement of the distance resolution leads to reducing the width $\tau e$, or, which amounts to the same, to increasing the spectral width of the radiated signal.

In such apparatus, the signal/noise ratio solely depends on the energy received by the target. Said energy, save for a factor k depending on the conditions of the medium, is that radiated by the transmitter, that is to say, that it corresponds to the product of the pulse power rating and the transmission time $\tau e$. The improvement of the signal/noise ratio leads to increasing the energy, which can only be done by increasing the pulse power rating from the moment when the width $\tau e$ is determined as a function of the choice of the distance resolution. But the pulse power rating is limited by the bursting energy of the transmitters, i.e. their present technological characteristics, and by any disadvantages that can result therefrom, from a biological standpoint.

In the aforesaid case of application, this alternative raises insuperable problems because, for this kind of apparatus to offer a really useful signal/noise ratio, it would be necessary, in view of the technical and biological limitation of the transmission pulse power rating, to increase the width $\tau e$, but then the distance resolution decreases, and this is a major disadvantage with an external apparatus used for measuring the blood flow rate, considering that great accuracy is needed in the search for echos.

Another problem arising with such apparatus, resides in the fact that they recurrently radiate the same wave train and that, as a result, a received echo cannot be identified in relation to its generator wave train. As a result, there is an ambiguity on the distance at which is situated the target. It is conceivable that such a problem could be settled by adopting a low repetition rate, when transmitting repeated wave trains. This would also have the advantage of conferring to the apparatus an increased scanning depth, this being definite advantage for an external measuring apparatus in the present application. However, it is also a known fact that the DOPPLER low frequency signal is sampled to the repetition rate of the radiated wave train and that, to reduce the velocity ambiguity, it is necessary to increase the repetition rate, and this is in contradiction with what is proposed hereinabove.

In the pulsed transmission type velocimeters, the DOPPLER low frequency signal corresponding to the fixed targets is a continuous signal and therefore can easily be eliminated at reception, by filtering, so as to leave only the variable signal of the moving target, and this represents an advantage.

In order to solve the aforesaid problems, velocimeters have been proposed which transmit continuously a random noise. With this type of apparatus, as with the pulsed transmission apparatus, the distance resolution only depends on the spectral width of the radiated signal, this being an easily controllable parameter.

With the said apparatus, the echo signal sent back is correlated with the radiated signal which is delayed by a value equal to the time taken by the ultrasounds to travel the return distance between the transmitter and the target. The choice of the delay therefore makes it possible to determine the scanning depth.

After each correlation period, a point is obtained which determines the DOPPLER low frequency curve, then another correlation is done for a similar period. The radiated signal not being a repeated signal, the distance ambiguity is rejected to infinity, or, which amounts to the same, there is no ambiguity despite the repeated correlation period.

The selection of the correlation period is determined as a function of the maximum velocity of the target meant to be detected, and therefore, this selection is effected so that the velocity ambiguity is greater than the said maximum velocity.

In the aforesaid apparatus, the energy returned during the correlation time is, for an equal pulse power rating, greater than that received in the case of pulsed transmission velocimeters, this giving a considerable improvement of the signal/noise ratio. This may appear as the positive aspect of these apparatus but, in reality, it has been found that the aforesaid gain does not allow them to be validly used in the considered application. Indeed, although the signal/noise ratio is good, the actual signal is composed of the echo coming from a moving target and of any echos coming from fixed targets. In the proposed application, the signals radiated by the fixed interfaces, such as the arteries walls, do not correspond, as in the case of the pulsed transmission velocimeter, to a continuous echo, since the transmitter signal is a random noise and, as a result, these signals cannot be filtered at reception to leave only the echo of a moving target subsisting. Consequently, although such apparatus show a considerable increase of the signal/noise ratio, they can only be used for measurements relative to a target moving inside a medium giving no fixed echos, and absolutely not for measuring the velocity of the blood flowing in the vessels.

In order to overcome the aforesaid disadvantage, another type of velocimeter has also been proposed which gives out a continuous pseudorandom noise. Such an apparatus has the same signal/noise ratio as the preceding type and a distance resolution given by the transmission band of the radiated signal.

Such an apparatus sends a repeated code in continuous manner and, as with the preceding type, a correlation of the received signal with the delayed radiated signal is done for a period which corresponds to the code. Considering that the code is repetitive, the signal received from the fixed echos is constant in level and can easily be filtered at reception, which in the present application, is an advantage over the noise velocimeters. However, since the transmitted code is repetitive, it is also conceivable that the problems of distance and velocity ambiguities can arise with these apparatus as they do with the pulsed transmission apparatus, and consequently, that said apparatus cannot validly be used for the external measurement of the blood flow.

The present invention relates to an apparatus of the aforesaid type and proposes a new measuring method and a new apparatus to carry it out, with which the advantages of good signal/noise ratio, good distance resolution and of having the possibility of filtering the fixed echos are retained, whilst offering the possibility of controlling, to an acceptable extent, the distance ambiguity without interfering with the velocity ambiguity.

The invention proposes a new measuring method whereby the transmission time of the pseudorandom signal is dissociated from the correlation time between such a delayed signal and the echo signal, so as to reduce the distance ambiguity for a given velocity ambiguity, and vice versa.

The invention thus permits a practical application of a DOPPLER velocimeter to the measurement of the blood flow rate, such a measurement being effected by simple external application of the apparatus, whatever the target considered and its location in the body.

According to the invention, the method for measuring the movement velocity of a target, using the DOPPLER effect, consisting in sending a pseudorandom ultrasonic signal in the direction of the target, collecting the returned echo, correlating for a given time the radiated signal and the echo received in order to obtain a value corresponding to a point which will determine the resulting DOPPLER low frequency curve, then in repeating successively the same operations in order to draw, with the succession of points obtained, the said resulting low frequency curve, is characterized in that a continuous pseudorandom noise is sent towards the target, which noise if formed by a repetitive code, is composed of n different elementary segments, in that a correlation is effected between the received echo and the delayed transmitted signal by proceeding successively for each elementary segment, using a different measuring band, in that the said correlation is effected for a period equal to the period of each segment, in that the correlation value(s) is/are collected and stored, and finally in that the DOPPLER low frequency curve is reconstituted by re-grouping the correlation values corresponding to the different elementary segments of the repetitive code.

According to the invention, the apparatus used to carry out the method comprises a first generator of a continuous pseudorandom noise which feeds an ultrasonic transmitter combined with a reception amplifier with as many outputs as there are elementary segments composing the repetitive code sent by the generator, a second generator, identical to the first and switched on by a control device with an output connecting it to the first generator and an output with a timing device connecting it to the second generator, n bands for independent measurement, connected on the one hand, to the reception amplifier, on the other hand to the second generator, and also to a sampler with a memory feeding through a filter a summation apparatus delivering in output the reconstituted DOPPLER low frequency curve.

The invention will be more readily understood on reading the following description given in reference to the accompanying drawings, in which:

FIGS. 1, 2a–2b, 3a–3b, and 4 are curves illustrating the phases in the method according to the invention, FIG. 5 is an overall diagram of an apparatus for carrying out the method according to the invention.

The method according to the invention consists in sending, towards a moving target, a continuous pseudorandom ultrasonic noise formed by the same repeated code C such as shown in FIG. 1. Said code is composed of a plurality of coded and different elementary segments $S_1$–$S_n$, always in the same order of succession and, in the illustrated example, having each the same length or transmission period d. The lengths d can be different, provided however that the longest length d is chosen to be, pursuant to SHANNON's theorem, at the most equal to half the detectable maximum frequency, so that the velocity ambiguity is greater than the maximum velocity to be measured. In this way, a positive answer is found to the problem of velocity ambiguity in the desired range of measurements.

The code C thus has a transmission period D which is equal to the product of d by the number n of elementary segments S, i.e. nd. In the illustrated example, the code C is composed of two elementary segments $S_1$ and $S_2$ which are shown as being formed by a binary combination, but which is reversed from $S_1$ to $S_2$. Of course, other combinations can be adopted and the code C can be composed of more than two elementary segments.

Then, according to the invention, the echo received is correlated with the radiated signal which is delayed by a value selected in relation to the desired scanning depth, but by operating in successive phases for each elementary segment and by using for each one a different measuring band. For example, assuming that the transmitted code Ca is composed, as illustrated in FIG. 1, of two elementary segments $S_1$ and $S_2$ a first correlation is effected of the segment $S_1$ of the received echo with the segment $S_1$ of the delayed transmitted signal, for a period $T_1$ (FIGS. 2) which is equal to the transmission period d, via a measuring band $V_1$ which is proper to the said segment $S_1$. This makes it possible, at the end of the correlation to obtain in the illustrated example, a value $Pa_1$ (FIG. 2a) corresponding to a moving target and/or a value $pa_1$ corresponding to a fixed target (FIG. 2b).

Immediately after, is effected the correlation of the segment $S_2$ of the received echo with the segment $S_2$ of the transmitted signal for a period $T_2$ (FIGS. 3) equal to d via a measuring band $V_2$ which is proper to $S_2$. This makes it possible, at the end of the correlation, to obtain, for example, the value $Pa_2$ (FIG. 3a) for the considered moving target and the value $pa_2$ (FIG. 3b) for the considered fixed target.

The correlation of the segment $S_1$ of the second code Cb is thereafter repeated for a period $T_1$, still via the band $V_1$, thereby permitting the values $Pb_1$ and $pb_1$ to be obtained. The procedure is the same for the segment $S_2$ in order to obtain the values $Pb_2$ and $pb_2$ and thus to define the data of the second code Cb.

The procedure is identically repeated for all the successive codes C.

The different correlation phases are thus at the origin of curves $c_1$ and $c_2$ defined by the succession of points $Pa_1 \ldots Pn_1$, and $Pa_2 \ldots Pn_2$ as far as the moving target is concerned, and/or of curves $l_1$ and $l_2$ defined by the succession of points $pa_1 \ldots pn_1$ and $pa_2 \ldots pn_2$ as far as the fixed target is concerned.

It is noted that the points $p_1 \ldots p_2$ of the curves $l_1$ and $l_2$ corresponding to a fixed target are aligned, considering the repetitive nature of the segments $S_1$ and $S_2$ and, consequently, in those cases when these points are simultaneously collected at points $P_1 \ldots P_2$ corresponding to a moving target, the only one meant to be measured, they can easily be eliminated by filtering so as to leave only the DOPPLER low frequency curves $c_1$ and $c_2$ subsisting.

Another step of the method consists then in reconstituting the resulting DOPPLER low frequency curve $c_r$ (FIG. 4) by the succession of points $P_1$ and $P_2$ which represent sampling values of the curve at the frequency of succession of the segments S.

It is clear from the foregoing that, the measuring method according to the invention makes use of a correlation time T which is equal to the transmission time of a coded segment and selected as a function of the maximum velocity which has to be detected, and of at least one other correlation time relative to a second and different coded segment composing, with the first, a repetitive code. Thus are dissociated the correlation time and the repetitive succession of the code constituting the pseudorandom ultrasonic sound. There results therefore a dissociation of the velocity and distance ambiguities and the possibility of acting independently on the parameters of each one. In the illustrated case, it is possible to fix T in relation to the maximum velocity to be detected and to reject the distance ambiguity when it is double that which would normally be linked to the correlation time T for a conventional apparatus giving a pseudorandom noise. The rejection factor of the distance ambiguity is therefore dependent on the number of elementary segments S which compose the repetitive code C.

Thus it becomes practical, which was not so with the known apparatus, to use a DOPPLER effect velocimeter, applied externally, for measuring the blood flow rate and for selecting the useful scanning depth whilst retaining the benefit of a low velocity ambiguity, of a good distance resolution, of a good signal/noise ratio and also of an easy elimination possibility of the echos produced by the fixed targets. In other words, the invention offers a solution to the problem of distance ambiguity and of scanning depth whilst re-grouping all the advantages offered separately by the previously known methods and apparatus and moreover it permits the use of such an apparatus for measuring the velocity of slightly reflecting moving particles because of the good signal/noise ratio.

By way of indication, when using the method for measuring the blood flow rate inside the human body, the following values should be taken into account:

ultrasonic frequency: 5 MHz pseudorandom noise pass band: 1 MHz more or less on either side of 5 MHz.

Period D of code C: 0.1 ms

Correlation time period d: 0.05 ms.

FIG. 5 gives an overall diagram of an apparatus for carrying out the method according to the invention. In the illustrated example, the apparatus comprises a generator 1 of a pseudorandom noise based on the repetitive code C, phase-modulating a sinusoidal generator of which the output, equipped with an amplifier 2, feeds a transmitter assembly 3 having an output associated to an amplifier 4. The generator 1 is started off with a device 5 controlling the repetition and evolution cycle of the transmission period D. The device 5 also controls, by means of an adjustable timing device, the delayed action of a generator $1a$ which is identical to the generator 1 and also transmits end-of-transmission information on segments S by as many outputs 6 as there are segments S, i.e. in the present case, two outputs $6_1$ and $6_2$. The generator $1a$ is connected to two correlators $7_1$ and $7_2$ which form part of the treatment bands $V_1$ and $V_2$ and are connected to the outputs of amplifier 4. The correlators $7_1$ and $7_2$ are respectively connected to a sampler with memory $8_1$–$8_2$ the output of which is provided with a filter $9_1$–$9_2$. The outputs of filters $9_1$–$9_2$ arrive into summation device 10 supplying the reconstituted DOPPLER low frequency signal, after the filtering of the fixed echos, from information released by the memory samplers $8_1$–$8_2$.

It should be noted that the code C can be sent directly to the transducer.

The invention is preferably applied to measuring the blood flow rate by means of an external apparatus. However other applications may be considered and the method according to the invention may be used whenever it is necessary to detect a moving target inside a medium having fixed targets.

The invention is not limited to the embodiment hereinabove described and illustrated in detail, and various modifications may be made thereto without departing from its scope. For example, it is possible to use only one transducer, transmitter and receiver, provided that the transmission does not last throughout the whole cycle.

What is claimed is:

1. A method for measuring velocity and distance of a moving target within a conveying medium comprising the steps of:

generating a continuous pseudorandom ultrasonic noise signal formed of a repetitive code composed of a plurality of different elementary segments;

transmitting said continuous pseudorandom ultrasonic noise signal generated in the direction of a target;

developing a delayed continuous pseudorandom ultrasonic noise signal corresponding to said continuous pseudorandom ultrasonic noise signal generated and delayed by a value representative of the distance to be scanned;

receiving echo signals from said moving target and said conveying medium;

correlating each different elementary segment in said received echo signals with corresponding elementary segments in said delayed continuous pseudorandom ultrasonic noise signal in a sequence corresponding to a sequence in which each of said plurality of different elementary segments in said echo signals are received to obtain a correlation value for each of said plurality of different elementary segments in said received echo signals, said correlation of each different elementary segment received with a corresponding elementary segment in said delayed continuous pseudorandom ultrasonic noise signal being conducted with a different measuring band for each of said plurality of different elementary segments and for a period equal to the period of that segment;

storing said correlation value obtained for each of said plurality of different elementary segments in said received echo signals; and reconstituting a DOPPLER low frequency signal from the correlation values stored by reading out said stored correlation values and grouping the same in a manner corresponding to said plurality of different elementary signals in said repetitive code.

2. The method according to claim 1 wherein said correlation value obtained for each of said plurality of different elementary segments in said received echo signals is stored in a memory and said step of reconstituting a DOPPLER low frequency signal includes additionally the step of filtering to remove constant values associated with received echo signals from said conveying medium.

3. The method according to claim 1 or 2 wherein said plurality of different elementary segments composing said repetitive code includes at least two elementary segments having a corresponding duration and a code pattern having a plurality of code elements therein set forth in a sequence, the code elements of one of said two elementary segments being reversed in sequence from the code elements present in the remaining one of said elementary segments.

4. The method according to claim 3 wherein said duration of said plurality of different elementary segments is selected as a function of the highest velocity to be detected.

5. Apparatus for measuring velocity and distance of a moving target within a conveying medium comprising:

first means for generating a continuous pseudorandom ultrasonic noise signal formed of a repetitive code composed of a plurality of different elementary segments;

means for transmitting said continuous pseudorandom ultrasonic noise signal to said moving target and said conveying medium;

receiver means for receiving echo signals from said moving target and said conveying means, said receiver means having one output for each of said plurality of different elementary segments in said repetitive code;

second means for generating a continuous pseudorandom ultrasonic noise signal identical to that generated by said first means, said second means for generating being selectively actuatable and having at least one output for each of said plurality of different elementary segments;

control means interconnected to said first and second means for generating for selectively actuating said first and second means for generating to develop a delayed continuous pseudorandom ultrasonic noise signal from said second means corresponding to said continuous pseudorandom ultrasonic noise signal generated by said first means and delayed therefrom by a value representative of the distance to be scanned;

a plurality of correlation means corresponding in number to said plurality of different elementary segments in said repetitive code, each of said plurality of correlation means being connected to a corresponding one of said outputs from said receiver means and said second means for generating to form a separate band for each of said plurality of different elementary segments;

a plurality of sampling means, each of said plurality of sampling means being connected to one of said plurality of correlation means to receive correlation values to be sampled therefrom;

a plurality of filter means for removing constants in each of said correlation values representing echo signals from said conveying medium, each of said plurality of filter means being connected to one of said plurality of sampling means; and summing means connected to each of said plurality of filter means for reconstituting a DOPPLER low frequency signal from the correlation values sampled by said plurality of sampling means.

6. The apparatus according to claim 5 wherein said second means for generating additionally produces end-of-transmission information for each of said plurality of different elementary segments to said repetitive code.

7. The apparatus according to claim 6 additionally comprising means for applying end-of-transmission information for each of said plurality of different elementary segments from said second means for generating to respective ones of said plurality of sampling means.

* * * * *